United States Patent [19]
Liu

[11] Patent Number: 5,570,447
[45] Date of Patent: Oct. 29, 1996

[54] AQUEOUS FLUID CORE WAVEGUIDE

[75] Inventor: Su-Yi Liu, Sarasota, Fla.

[73] Assignee: World Precision Instruments, Inc., Sarasota, Fla.

[21] Appl. No.: 516,158

[22] Filed: Aug. 17, 1995

[51] Int. Cl.$^6$ .................................................. G02B 6/20
[52] U.S. Cl. ................................... 385/125; 385/128
[58] Field of Search ................................... 385/125, 141, 385/145, 142

[56] References Cited

U.S. PATENT DOCUMENTS 5,221,387  7/1993  Robbins et al. ..................... 385/125
5,267,341  11/1993  Shearin ............................... 385/125

*Primary Examiner*—John Ngo
*Attorney, Agent, or Firm*—Chilton, Alix & Van Kirk

[57] ABSTRACT

Water or some other aqueous fluid is employed as the light transmitting medium of a liquid core fiber-optic waveguide cell by employing, to define the core region, a waveguide vessel having an exterior coating composed of a material having a refractive index of less than 1.33. The light conducting channel defined by the aqueous fluid filled core may be a capillary or other suitably shaped vessel.

18 Claims, 2 Drawing Sheets

AQUEOUS FLUID CORE WAVEGUIDE

FIELD OF THE INVENTION

The present invention relates to the use of water or some other aqueous liquid as the light conducting core medium of an elongated, small diameter vessel employed for light transmission. More particularly, this invention is directed to tubular light guides suitable for spectrometry, photometry and fluorimetry. Accordingly, the general objects of the present invention are to provide novel and improved methods and apparatus of such character.

BACKGROUND OF THE INVENTION

While not limited thereto in its utility, the present invention has applicability to the field of fiber optics. Liquid core fiber-optic waveguides, i.e., light guide fibers in the form of a capillary filled with a fluid which functions as the light transmitting core, have previously been proposed. For a first example of such a prior liquid core fiber-optic waveguide, reference may be had to U.S. Pat. No. 3,894,788. Since light cannot be efficiently propagated through a fluid filled capillary unless the refractive index of the capillary is less than that of the core fluid, the waveguides of U.S. Pat. No. 3,894,788 use an organic fluid as the core liquid. These organic fluids are specially selected so as to have refractive indices which are greater than that of the particular material from which the capillary is fabricated in order to permit long distance propagation of light waves through the core liquid.

A second example of a prior liquid core fiber-optic waveguide is an uncoated quartz or glass tube containing water. The interface between the outer surface of the tube and the air provides the "total reflection" surface which defines the waveguide. Such waveguides have limited practical application because the reflection surface is easily contaminated by contact with other components, finger prints or dust. In addition, the long tubes require thick tube walls due to the brittleness of the tube materials. Thick tube walls create a nonlinearity in light absorption spectroscopy because a higher proportion of the light travels in the tube wall rather than in the fluid core.

There has been a long standing desire to employ water or some other aqueous fluid in a liquid core fiber-optic environment for the purpose of facilitating chemical analyses of aqueous solutions by light interactive processes. A variety of techniques are available for use in the analysis of fluid samples. These techniques include optical methodology, particularly photometry and spectrophotometry, wherein the composition and concentration of dissolved substances are determined by measuring the absorption of light in a liquid which includes such substances. These optical analysis techniques are based on the fact that different substances will absorb light at different wave lengths. In the practice of these optical techniques, light absorption at discrete wave lengths or over a broad light spectrum, including ultraviolet, visible or infrared spectra, may be measured.

The need for instruments capable of the optical analysis of aqueous samples in the sub-milliliter volume range has grown in recent years. An important reason for this growing need is the fact that protein and DNA specimens are usually procured in small volume aqueous samples. For example, it is often difficult to obtain large amounts of animal, especially human, tissue samples for analysis. It is also costly to synthesize or purify protein, enzyme, antibody and DNA samples in large amounts.

Conventional absorption spectrometers are not sufficiently sensitive to analyze solutions prepared from the very small volume samples discussed above. For example, the approximate detection limit, defined as the lowest concentration that can be distinguished from background signal for double stranded DNA using absorption at a wave length of 260 nm is about 250 nanograms for a 0.5 ml, 10 mm light path length cuvette.

There have been efforts to reduce the requisite sample cuvette volume. Such efforts have often been characterized by a reduction in the light path length which, in turn, reduces instrument sensitivity. The smallest commercially available fluid sample cuvettes with 10 mm long light paths typically contain fluid volume in the 30 µl to 50 µl range. For a 5 µl volume cell, however, the path length would be limited to 0.5 mm and thus unsatisfactory for analysis.

U.S. Pat. No. 5,416,879 which is assigned to the assignee of the present invention, discloses a liquid core fiber-optic waveguide to which the present invention relates. In a preferred embodiment, the waveguide is fabricated from an amorphous polymer material having a refractive index which is lower than that of water. Alternatively, the polymer material may be coated on the internal wall of a suitably prepared rigid tube comprised of glass or the like. The only currently available material having a refractive index less 1.33, which is chemically inert and insoluble in water, is a fluoropolymer, TEFLON AF™. In certain applications this material has several shortcomings that may cause optical losses in the waveguide. The polymer is soft and may be easily scratched, adversely affecting its properties as a mirror surface. The polymer is also hydrophobic. Consequently air bubbles and less polarized molecules in aqueous solutions may stick to the surface of the tube.

SUMMARY OF THE INVENTION

The present invention overcomes the above-briefly discussed and other deficiencies and disadvantages of prior art liquid core, fiber-optic waveguides. In doing so, the present invention provides a waveguide in the form of a rigid aqueous liquid filled capillary, or other suitably shaped inflexible vessel, which may be filled with an aqueous liquid.

In accordance with a preferred embodiment of the present invention, a suitably shaped vessel, i.e., a rigid waveguide, is fabricated from a glass or quartz which is coated on its outside surface with a material having a refractive index less than that of water. The resulting vessel will be of tubular construction and will be inflexible under the normal conditions of use to be described.

The coating functions as the total reflection surface and is protected by the tube walls from contamination or abrasion by the aqueous solution. The total reflective coating may be encased in a second coating or tube to prevent mechanical wear or damage. Placing the total reflection surface on the exterior of the tube also permits the novel use of a group of inorganic materials as the reflective coating. These materials have very low refractive indices but may be soluble in the aqueous solution.

BRIEF DESCRIPTION OF THE DRAWING

The present invention may be better understood and its numerous objects and advantages will become apparent to those skilled in the art by reference to the accompanying drawings wherein like reference numerals refer to like elements in the several figures and in which.

DETAILED DESCRIPTION OF THE DISCLOSED EMBODIMENTS

In order to propagate light with negligible losses through an optical fiber, it is necessary to channel the light through a light conducting core region which is surrounded or clad by a material having a lower refractive index to the light than the material comprising the core. This arrangement results in most of the light which seeks to escape through the wall of the light conductor being reflected and, therefore, confined within the core region provided, of course, that the incident light is introduced into the core material within an appropriate acceptance angle relative to the axis of the core. Most present day solid optical fibers are comprised of special silica or glass cores which are clad with thin outer coatings of silica or other materials of lesser refractive index than the core material. Solid polymer cores with cladding are also widely used. The polymer clad fibers are usually employed for relatively short distance transmission while the clad glass core fibers are typically used for longer distance light propagation.

As discussed above, the use of water as a core material has heretofore been confined limited because of limitations the characteristics of in the materials available for use as the reflective surface and/or the body of the waveguide. In this regard, it should be noted that, prior to the present invention, it had been believed that the total reflection surface had to be in direct contact with the core liquid to provide the proper light propagation within the waveguide.

In the practice of the present invention, a rigid body defining a channel for containing a liquid core 30, for example a capillary, is defined by a tube 40 composed of glass, quartz, transparent polymers such as polymethyl methacrylate (PMMA), polyvinylidene fluoride (PVDF) and ethylene tetrafluorothylene (ETFE), or similar material. The wall thickness of the tube wall 40 should be minimized to limit the amount of light that is propagated within the tube wall, the wall having been indicated at 42. However, a minimum wall thickness of 50 microns is preferred to maintain tube rigidity for glass and quartz embodiments.

Figure 2:
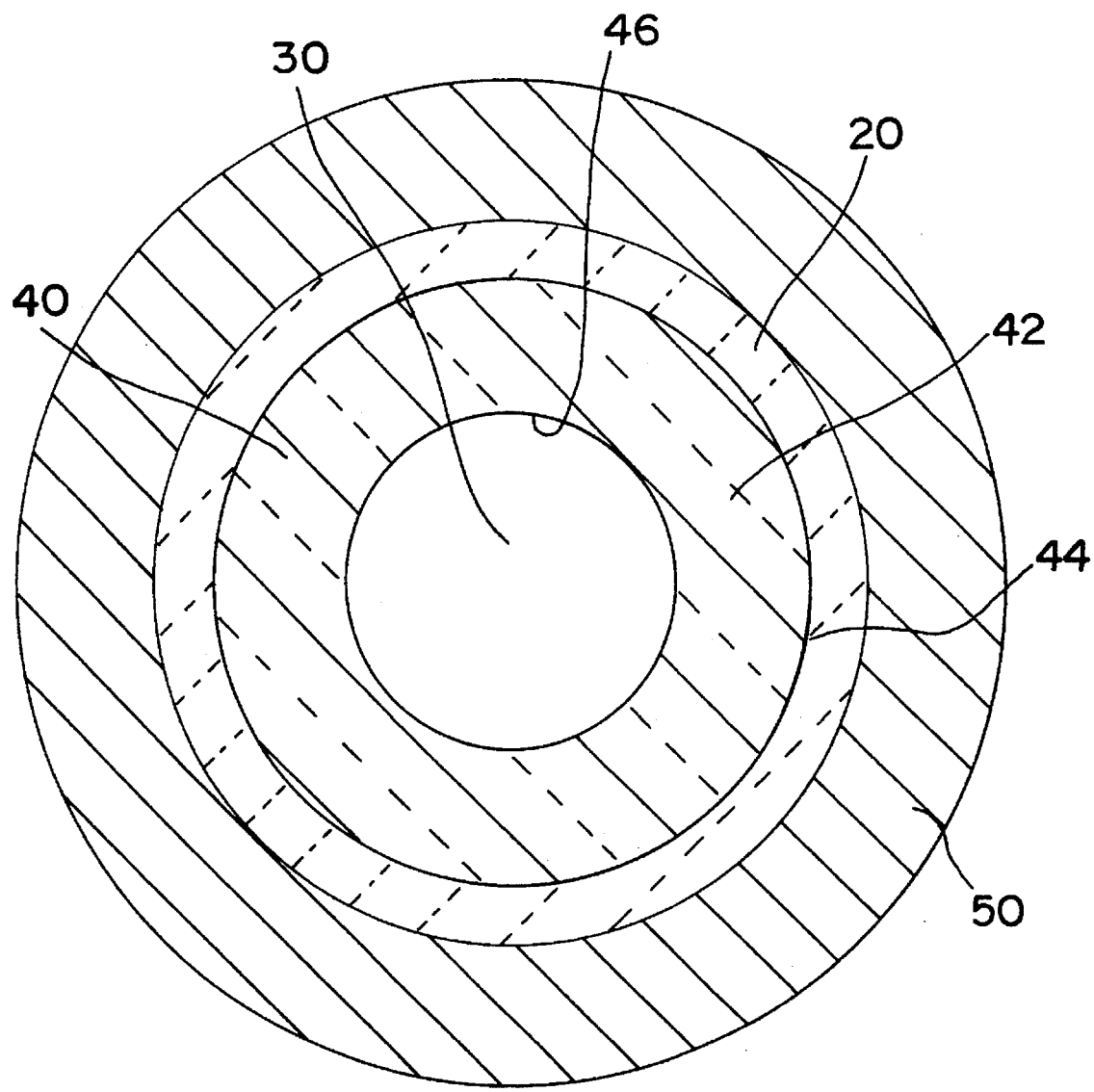
FIG. 2 is a cross section view of an alternate embodiment of the waveguide of FIG. 1.

A material which possess a refractive index which is less than 1.33 is used to coat the exterior surface of the tube. The coating 20 preferably has a thickness of at least four (4) times the wavelength of the light to be propagated by the waveguide. The coating 20 may be applied by dipping, spraying or other means known in the art. Referring to FIG. 2, a protective outer coating or jacket 50 of stainless steel or other suitable material may be employed to protect the coating material from scratching and mechanical abrasion.

Amorphous polymers with sufficiently low refractive indices to permit use as coating 20 can be created if their structural elements include some or all of the fluorocarbon groups —$CF_3$, —$CF_2O$, —$CF(CF_3)_2$ and —$CH(CF_3)_2$. A commercially available fluorocarbon material having a refractive index which is suitable for use in the practice of the present invention is sold by the Dupont Company under the trademark "Teflon AF". This commercially available fluorocarbon material has a refractive index in the range of approximately 1.29 to 1.31.

Placing the total reflection surface 22, i.e., the interface between coating 20 and the exterior surface 44 of tube 40, exteriorly of the tube 40 also allows the use of a group of inorganic materials that have very low refractive indices, but are soluble in the core liquid 30, for coating 20. These materials may include beryllium fluoride glasses such as $BeF_2$, $BeF_2$—$RbF$, $BeF_2$—$KF$, $BeF_2$—$LiF$, $BeF_2$—$NaF$, and fluorophosphate glasses. Such materials are soluble in water and therefore could not have been considered for use in waveguides such as disclosed in U.S. Pat. No. 5,416,879. Such materials may exhibit a greater resistance to scratching and mechanical abrasion, making the protective sleeve 50 unnecessary.

Placing the reflection surface 22 on the exterior surface 44 of the tube 40 allows the interior surface 46 of the tube 40 to be modified to reduce the adhesion or retention of molecules in the liquid due to surface potential. For example, a silanization procedure may be used to change the charge on the interior surface 46 from negative to neutral or positive.

As will be described below, an external light source, schematically indicated at 12, can be coupled to the aqueous core material 30 of a capillary or vessel formed in accordance with the invention simply by inserting a solid optical fiber into the core fluid 30. Thus, in the practice of the invention, the light is directly launched into the liquid 30 and not into the wall 42 of tube 40.

Figure 1:
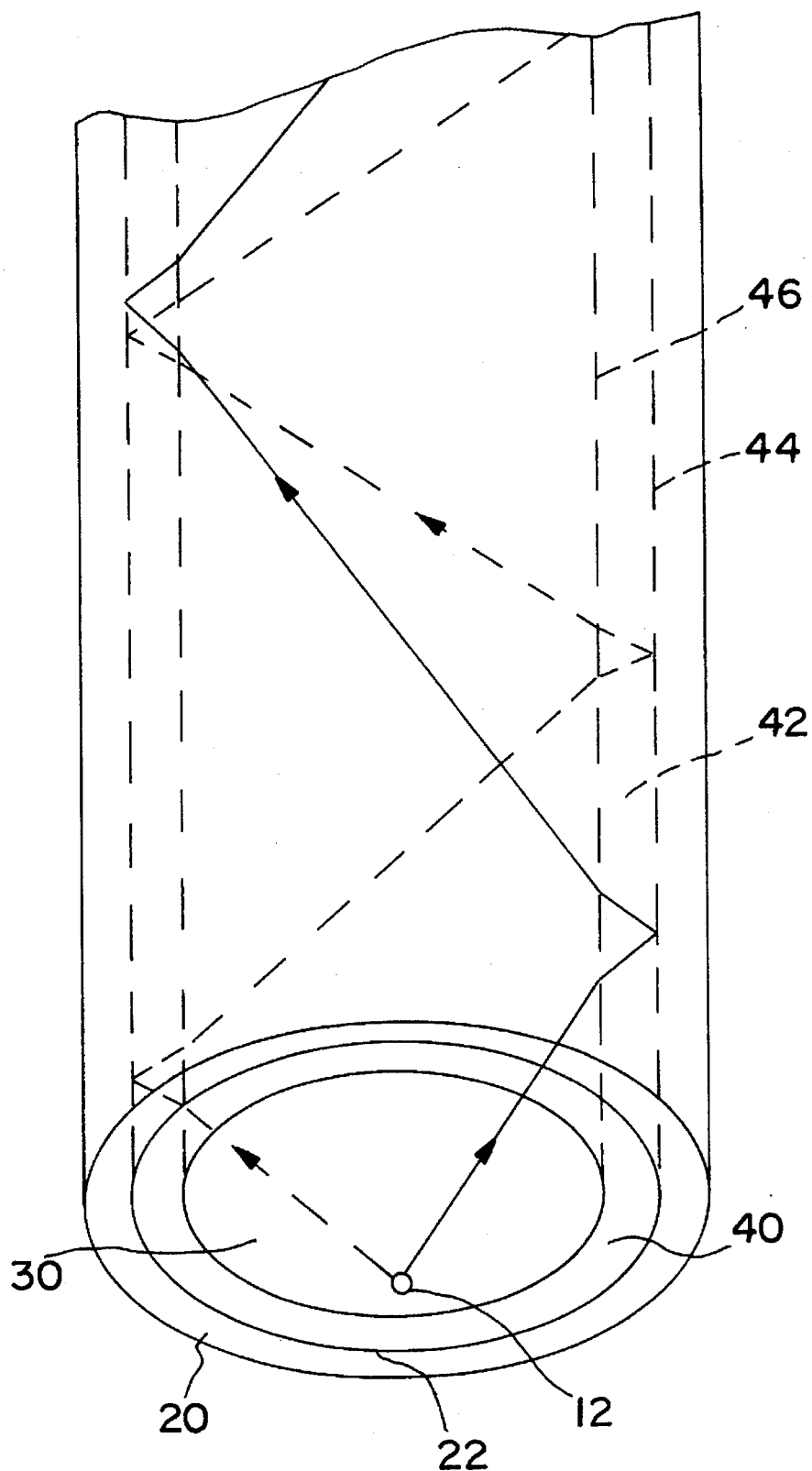
FIG. 1 is a schematic showing of a portion of a waveguide fabricated in accordance with the present invention.

Referring to FIG. 1, and presuming light source 12 to be the end of an optical fiber inserted into core liquid 30, the transmitted path of light emanating from a point source 12 is the sum of the many small multiple reflections from the reflection surface 22 as the light advances along the waveguide 10.

As will become apparent, waveguides 10 in accordance with the present invention may be employed to optically analyze solutes dissolved in water by transmitting ultraviolet, visible or infrared light through the aqueous sample. The applied light beam can advance a greater distance through the analyte fluid confined in the core region of a waveguide in accordance with the invention because most of the light which seeks to escape through the tube wall is totally reflected by the reflection surface. Therefore, the effective length of the light path through the core fluid is increased. The increase in the light path, in turn, greatly increases the achievable sensitivity of a fluid analysis technique such as light absorption, colorimetry, or fluorescence because of the increased amount of light interaction with the aqueous fluid analyte.

A further advantage of the present invention is that it permits the analysis of minuscule amounts of liquid analyte samples because the containing capillary can have an inner diameter as small as 0.1 millimeter or less. Fluid samples with volume as little as 1 microliter or less can be directly analyzed in such small diameter capillaries by illuminating the core sample with light of appropriate wave lengths.

As explained above, during use of the invention in a fluid analysis procedure, emitted light is transmitted to an aqueous solution which is disposed in the waveguide. The waveguide causes the received light to be propagated axially through the fluid. In accordance with the present invention, the capillary configuration of the waveguide maximizes the light path for any given fluid volume.

While preferred embodiments have been described, various modifications and substitutions may be made thereto without departing from the spirit and scope of the invention. Accordingly, it is to be understood that the present invention has been described by way of illustration and not limitation.

What is claimed is:

1. Light transmission means comprising:

an aqueous fluid for transmitting light;

capillary means defining a core region, said aqueous fluid occupying said core region, said capillary means comprising a wall defining interior and exterior surfaces, said capillary means being rigid and having a refractive index which is greater than or equal to the refractive index of said aqueous fluid, said aqueous fluid being in contact with said interior surface; and coating means for coating said exterior surface of said capillary means, said coating means having a refractive index which is less than the refractive index of said aqueous fluid.

2. The light transmission means of claim 1 wherein said coating means has a refractive index which is less than 1.33.

3. The light transmission means of claim 2 wherein light waves are lunched into in said aqueous fluid, said light waves having a maximum wavelength, said coating having a thickness equal to at least four times said wavelength.

4. The light transmission means of claim 2 wherein said coating means comprises an amorphous solid fluorocarbon material.

5. The light transmission means of claim 2 wherein said coating means comprises a beryllium fluoride glass.

6. The light transmission means of claim 2 wherein said coating means comprises a beryllium fluoride glass selected from the group consisting of $BeF_2$, $BeF_2$—$RbF$, $BeF_2$—$KF$, $BeF_2$—$LiF$, and $BeF_2$—$NaF$.

7. The light transmission means of claim 2 wherein said coating means comprises a fluorophosphate glass.

8. The light transmission means of claim 1 further comprising jacket means disposed around said coating means for protecting said coating means from mechanical degradation.

9. The light transmission means of claim 8 wherein said jacket means comprises a stainless steel sleeve.

10. The light transmission means of claim 1 wherein said capillary means is composed of glass.

11. The light transmission means of claim 1 wherein said capillary means is composed of quartz.

12. The light transmission means of claim 1 wherein said capillary means is composed of a transparent polymeric material.

13. The light transmission means of claim 1 wherein said capillary means is composed of polymeric material selected from the group consisting of polymethyl methacrylate, polyvinylidene fluoride, and ethylene tetrafluorothylene.

14. A method of employing an aqueous liquid as a light transmission medium, said method comprising the steps of:

forming a rigid channel comprising a wall having internal and external surfaces, the wall having a refractive index of at least 1.33;

coating the external surface of the wall with a material having a refractive index of less than 1.33;

filling the channel with an aqueous liquid whereby the liquid is in contact with the internal surface of the wall; and introducing light directly into the aqueous liquid at one end of the channel.

15. The method of claim 14 further comprising the step of covering the coating material with a protective jacket.

16. The method of claim 14 further comprising the step of modifying the electrical charge on the internal surface of the wall.

17. A liquid core optical waveguide comprising:

a rigid capillary tube, said tube being comprising of a material selected from the group comprising glass, quartz and transparent polymeric materials, said capillary tube comprising opposite ends and a wall having interior and exterior surfaces;

an aqueous solution disposed within said tube and in contact with the interior surface of the wall thereof;

a coating on said exterior surface of said capillary tube, said coating being comprised of a material having a refractive index which is less than that of water, said coating cooperating with said tube and aqueous solution to define the waveguide, the interface between said coating and said tube exterior surface defining a reflection surface for light being guided by said waveguide; and means for launching light into said aqueous solution at an end of said waveguide.

18. The wave guide of claim 17 further comprising:

a jacket disposed around at least a portion of said coating for protecting said coating from mechanical degradation.

* * * * *